(12) United States Patent
Nempont et al.

(10) Patent No.: US 10,820,874 B2
(45) Date of Patent: Nov. 3, 2020

(54) AUTOMATIC DEVICE-FOOTPRINT-FREE ROADMAPPING FOR ENDOVASCULAR INTERVENTIONS

(71) Applicant: KONINKLIJKE PHILIPS N.V., Eindhoven (NL)

(72) Inventors: Olivier Pierre Nempont, Suresnes (FR); Pascal Yves Francois Cathier, Suresnes (FR); Raoul Florent, Suresnes (FR); Guillaume Julien Joseph Pizaine, Suresnes (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1249 days.

(21) Appl. No.: 15/023,298

(22) PCT Filed: Sep. 9, 2014

(86) PCT No.: PCT/EP2014/069144
§ 371 (c)(1),
(2) Date: Mar. 18, 2016

(87) PCT Pub. No.: WO2015/039921
PCT Pub. Date: Mar. 26, 2015

(65) Prior Publication Data
US 2016/0228084 A1    Aug. 11, 2016

(30) Foreign Application Priority Data
Sep. 20, 2013  (EP) .................................... 13306286

(51) Int. Cl.
*A61B 6/00* (2006.01)
*A61B 6/12* (2006.01)
*A61B 6/04* (2006.01)

(52) U.S. Cl.
CPC ................ *A61B 6/504* (2013.01); *A61B 6/12* (2013.01); *A61B 6/461* (2013.01); *A61B 6/481* (2013.01);
(Continued)

(58) Field of Classification Search
CPC .......... A61B 6/504; A61B 6/461; A61B 6/481; A61B 6/487
See application file for complete search history.

(56) References Cited

U.S. PATENT DOCUMENTS

| | | |
|---|---|---|
| 5,056,524 A | 10/1991 | Oe |
| 7,826,884 B2 | 11/2010 | Baumgart |

(Continued)

FOREIGN PATENT DOCUMENTS

| | | |
|---|---|---|
| JP | 2010075554 A | 4/2010 |
| JP | 2012228592 A | 11/2012 |
| WO | 2012011035 A1 | 1/2012 |

OTHER PUBLICATIONS

Advanced Interventions in your Lab, Philips Allura XPER RD20 System Specifications, 2009.
(Continued)

*Primary Examiner* — Joseph M Santos Rodriguez

(57) ABSTRACT

A system (1) and a corresponding method enable an enhanced roadmapping visualization without unnecessary device-footprints. The system (1) includes an x-ray imaging device (3) for acquiring x-ray images and a calculation unit (5). The x-ray imaging device (3) is adapted for acquiring a first x-ray image (21) with an interventional device (17) present in the vessels (19) while no contrast agent is present in the vessels (19) and a second x-ray image (23) with the interventional device (17) present in the vessels (19) while contrast agent is present in the vessels (19). The calculation unit is adapted for creating a roadmap image (27) by subtracting the first x-ray image (21) from the second x-ray (Continued)

image (23) and automatically minimizing the visibility of the interventional device (17) in the roadmap image (27). A display unit (7) is adapted to display the roadmap image (27) or an overlay of a current fluoroscopy image (31) with the roadmap image (27).

15 Claims, 4 Drawing Sheets

(52) U.S. Cl.
CPC ............ *A61B 6/487* (2013.01); *A61B 6/5235* (2013.01); *A61B 6/5252* (2013.01); *A61B 6/0407* (2013.01); *A61B 6/4441* (2013.01); *A61B 6/463* (2013.01)

(56) References Cited

U.S. PATENT DOCUMENTS

| | | | |
|---|---|---|---|
| 2002/0045817 A1* | 4/2002 | Ichihashi | ............ A61B 6/4233 600/425 |
| 2007/0058781 A1 | 3/2007 | Nakano et al. | |
| 2009/0103682 A1 | 4/2009 | Chen | |
| 2010/0208973 A1* | 8/2010 | Lienard | .................... A61B 6/12 382/132 |
| 2010/0220917 A1 | 9/2010 | Steinberg | |
| 2011/0038458 A1 | 2/2011 | Spahn | |
| 2011/0249794 A1 | 10/2011 | Florent | |
| 2012/0230565 A1 | 9/2012 | Steinberg | |
| 2012/0277581 A1 | 11/2012 | Urushiya et al. | |
| 2012/0300903 A1 | 11/2012 | Yao et al. | |
| 2013/0034283 A1* | 2/2013 | Ohishi | .................... A61B 6/032 382/128 |

OTHER PUBLICATIONS

Schneider, Matthias et al "Automatic Global Vessel Segmentation and Catheter Removal using Local Geometry Information and Vector Field Integration", IEEE, 2010, pp. 45-48.

* cited by examiner

AUTOMATIC DEVICE-FOOTPRINT-FREE ROADMAPPING FOR ENDOVASCULAR INTERVENTIONS

CROSS-REFERENCE TO PRIOR APPLICATIONS

This application is the U.S. National Phase application under 35 U.S.C. § 371 of International Application No. PCT/EP2014/069144, filed on Sep. 9, 2014, which claims the benefit of European Patent Application No. 13306286.9, filed on Sep. 20, 2013. These applications are hereby incorporated by reference herein.

FIELD OF THE INVENTION

The present invention relates to roadmapping for endovascular interventions. In particular, the present invention relates to a system and a corresponding method for automatic roadmapping for endovascular interventions. Furthermore, the present invention relates to a computer program element and a computer readable medium.

BACKGROUND OF THE INVENTION

During endovascular procedures under x-ray guidance such as Endovascular Aneurysm Repair (EVAR) catheters and treatment devices are inserted in the vasculature though a small incision e.g. in the abdominal region. The user then moves the tools to the treatment area and treats the pathology under x-ray control.

Endovascular tools are usually radio opaque and very contrasted in fluoroscopic images. The vasculature is not visible but the injection of contrast agent allows temporarily visualizing of the vessels lumen. Several angiograms are usually acquired during such a procedure to control the position of the devices with respect to the anatomy.

To reduce the amount of injected contrast agent, roadmapping visualization may be used. For example, roadmapping is known from US 2011/0 249 794 A1. Anatomical information may be overlaid on live fluoroscopic images to allow the visualization of the anatomy without contrast agent. This may be achieved using pre-interventional exams, e.g. segmented CT, that are registered in the intervention room.

Furthermore, this also may be done based on previously acquired angiograms, if the position of the x-ray system has not been changed. In that case a mask image representing the vessels is computed from the reference angiogram. The mask image or roadmap image may for example correspond to an injected frame or to a subtracted image between an injected frame and a non-injected frame. The result may then be overlaid on live fluoroscopic frames bringing the vessels footprint on live images. This approach may provide great results when there is no motion of the objects in the images.

However, when there is some motion, for instance due to breathing, the mask image may contain a lot of artefacts. In particular, the artefacts may be caused by interventional devices present in the vessels during image acquisition. The resulting overlaid image may be not very helpful. For example, a moving device may generate a positive and a negative footprint in a mask image generated by subtraction. When the mask image is overlaid on fluoroscopic frames the device may appear three times. Moreover, those artefacts may often be located at the treatment area and may therefore occlude the visualization of the devices in the live overlaid frame.

This issue may be avoided by using as mask image an injected frame that is subtracted to the live frame. However, this restricts the acquisition protocols and/or dosage for angiograms and fluoroscopy, because the same acquisition protocols and/or dosage have to be used for both image sequences.

SUMMARY OF THE INVENTION

Thus, there may be a need to provide a system and a method which allows for an enhanced roadmapping visualization during endovascular interventions.

According to a first aspect of the present invention an imaging system for automatic roadmapping for endovascular interventions is provided. The system comprises an x-ray imaging device for acquiring x-ray images and a calculation unit. The x-ray imaging device is adapted for acquiring a first x-ray image with an interventional device present in the vessels while no contrast agent is injected into the vessels. Furthermore, the x-ray imaging device is adapted for acquiring a second x-ray image with the interventional device present in the vessels while contrast agent is injected into the vessels. The calculation unit is adapted for creating a roadmap image by subtracting the first x-ray image from the second x-ray image. Moreover, the calculation unit is adapted for automatically minimizing the visibility of the interventional device in the roadmap image.

In other words, the idea of the invention may be seen in providing a roadmap and possibly also a visualization of a roadmap that removes explicitly the devices footprint during the mask image generation. This allows for obtaining a useable roadmap when there is some motion of objects in the acquired images. In a first approach, for enhancing the quality of the roadmap image the footprint of the interventional device may automatically be detected in injected and non-injected frames of the angiogram or aortogram. Subsequently, the interventional device may be in-painted in each frame before generating the roadmap image. In a second approach, after subtracting the injected and non-injected frames from each other, the interventional device may be removed by filtering and saturating the roadmap image. In both approaches, the resulting roadmap image does not contain anymore the footprint of the interventional device, such that the treatment area is optimally visible.

Thus, the system advantageously allows for providing a device-free roadmap image showing the anatomy, i.e. the vessels. This, roadmap may e.g. be overlaid on live fluoroscopy images without occluding the visualization of the area of interest.

The system as well as the method may for example be employed in connection with aneurism treatment, heart valve replacement and stent placement by an imaging system e.g. in catheter laboratories. In particular, it can be employed in abdominal interventions, for the treatment of Aortic Abdominal Aneurysms (AAA). The interventional device visible in the images may for example be a wire or a catheter with a balloon and/or a stent or stent graft. Therein, the system as well as the method provides a roadmap, i.e. a frame or a frame sequence showing the anatomy without interventional devices, which may help in assisting a physician.

The first and the second x-ray images may for example be different frames or images of an angiography sequence. Both x-ray images show the interventional device in the vessels. However, in the first x-ray image no contrast agent is present in the area of interest, i.e. the area shown in the images. In the second x-ray image contrast agent is present. Furthermore, the first x-ray image may be subtracted from a plurality of second x-ray images. The plurality of second x-ray images may represent the angiography along the time axis where time t refers to a particular time and image.

Acquiring the first and second x-ray images by the x-ray imaging device may denote retrieving the images from a data base or a memory of a computer. Alternatively, acquiring may comprise detecting the images.

Therein, the subtracting of the first x-ray image from the second x-ray image takes place in the x-ray absorption domain. For example, subtracting may comprise forming a difference. Furthermore, subtracting may comprise applying the logarithmic function to the image pixel values, forming the difference of the pixel values of the first and the second x-ray images and applying the exponential function to the result. By subtracting the images, background structures such as bones are removed from the subtraction result.

Furthermore, automatically minimizing the visibility of the interventional device in the roadmap image may denote removing or wiping out the interventional device in the subtraction result. Automatically, may denote that the minimising of the visibility of the interventional device takes place without the necessity of the interaction with a user.

The calculation device may for example be a processor with a memory unit.

Therein, the calculation unit may comprise an algorithm e.g. stored and executed by the calculation unit for generating the roadmap image and minimizing the visibility of the interventional device.

According to an exemplary embodiment of the invention, the x-ray imaging device is adapted for acquiring at least one current, i.e. live fluoroscopy image with the interventional device inserted into the vessels. The calculation unit is adapted for generating a first composite image by combining the roadmap image with the at least one current fluoroscopy image. Therein, combining may comprise overlaying or adding the images. The acquisition geometry of the x-ray imaging device may be the same during the angiography and during the live fluoroscopy. The first composite image may represent or visualize on a display the current fluoroscopy image at a time t overlaid with the anatomy of the vessels.

According to a further exemplary embodiment of the invention, the x-ray imaging device is adapted for acquiring a reference fluoroscopy image with the interventional device present in the vessels. The reference fluoroscopy image may for example be the first frame of the fluoroscopy sequence. The calculation unit is adapted for automatically minimizing the visibility of the interventional device in the reference fluoroscopy image. Furthermore, the calculation unit is adapted for creating an enhanced current fluoroscopy image by subtracting the reference fluoroscopy image from the current fluoroscopy image. The enhanced current fluoroscopy image, i.e. the subtraction result, may represent the interventional device at time t possibly without surroundings and/or background. Moreover, the calculation unit is adapted for generating a second composite image by combining the roadmap image with the enhanced current fluoroscopy image. The second composite image may represent or visualize on a display the device at a time t overlaid with the anatomy of the vessels.

According to a further exemplary embodiment of the invention, the system further comprises a display unit which is adapted for displaying the enhanced current fluoroscopy image, the first composite image and/or the second composite image. The display unit may comprise one or several screens. The mentioned images may be shown simultaneously. Alternatively, one of the following images is visualized on the display unit: enhanced current fluoroscopy image, the first composite image and the second composite image.

According to a further exemplary embodiment of the invention, automatically minimizing the visibility of the interventional device comprises an automatic detection of the interventional device by the calculation unit in the first x-ray image, in the second x-ray image and/or in the reference fluoroscopy image. Moreover, automatically minimizing the visibility of the interventional device further comprises in-painting of the detected interventional device. Therein, in-painting may denote adapting the area of the interventional device to the surroundings. Furthermore, in-painting may denote matching the coloring or filling of the interventional device with the color of the background surrounding the interventional device. In-painting may also denote the modeling of the device absorption, the estimation of the model instance from the observations of the pixel values on the footprint of the device, and the subtraction of this model instance from image, thus restoring the background underneath the device. For instance, in the case of a catheter or a wire, the model may be an elongated tube of constant absorption. The tube footprint is output by the device automatic detector, and the value of the absorption is computed as the value that, once subtracted from the values of pixels of the device footprint, insures the best resulting background continuity between the surrounding pixels of the footprint and those over the footprint. Instead of a constant value, the elongated device absorption may also be modeled as a cross-section absorption profile, which may be estimated with a similar technique.

According to a further exemplary embodiment of the invention, the automatic detection of the interventional device is based on the contrast value of the interventional device in the first x-ray image, in the second x-ray image and/or in the reference fluoroscopy image. Alternatively or additionally, the automatic detection of the interventional device is based on the geometry of the interventional device in the first x-ray image, in the second x-ray image and/or in the reference fluoroscopy image. Particularly, the geometry may be an elongated object. Alternatively or additionally, the automatic detection of the interventional device is based on the kinetics of the interventional device in the first x-ray image, in the second x-ray image and/or in the reference fluoroscopy image. Particularly, as the wire is restricted to the inside of the vessel, a maximum speed and a largest motion in longitudinal direction, i.e. in parallel to the longitudinal axis of the vessel and/or of the interventional device may be used to identify the location of the device or tool.

According to a further exemplary embodiment of the invention, automatically minimizing the visibility of the interventional device comprises filtering out details smaller than the vessels in the first x-ray image, in the second x-ray image and/or in the reference fluoroscopy image by the calculation unit. For this purpose, e.g. morphological filtering may be employed. Alternatively, details smaller than the vessels are filtered out directly within the vessels and not in the complete images. In this case, automatically minimizing the visibility of the interventional device may further comprise automatically detecting the vessels, and particularly the vessel of interest. Therein, the vessel of interest may for example be the aorta, which may be the most dark and bulky object and/or the widest connected object in the images. Filtering out may comprise smoothing and/or saturating the area of the device.

According to a second aspect of the present invention, a method for automatic roadmapping for endovascular interventions is provided. The method may be applied in combination with an imaging system described above. The method comprises the following steps: acquiring by an x-ray imaging device a first x-ray image with an interventional device present in the vessels while no contrast agent is injected into the vessels; acquiring by the x-ray imaging device a second x-ray image with the interventional device present in the vessels while contrast agent is injected into the vessels; creating by a calculation unit a roadmap image by subtracting the first x-ray image from the second x-ray image; automatically minimizing by the calculation unit the visibility of the interventional device in the roadmap image. Therein, the order of the steps of the method may vary. For example, the visibility of the interventional device may be minimized by processing the first x-ray image and the second x-ray image before subtracting these images. Alternatively, the visibility of the interventional device may be minimized by processing the roadmap image after subtracting the first x-ray image from the second x-ray image.

According to a further exemplary embodiment of the invention, the method further comprises acquiring at least one current fluoroscopy image with the interventional device present in the vessels; and generating a first composite image by combining the roadmap image with the at least one current fluoroscopy image.

According to a further exemplary embodiment of the invention, the method further comprises acquiring a reference fluoroscopy image with the interventional device present in the vessels; automatically minimizing the visibility of the interventional device in the reference fluoroscopy image; creating an enhanced current fluoroscopy image by subtracting the reference fluoroscopy image from the current fluoroscopy image; and generating a second composite image by combining the roadmap image with the enhanced current fluoroscopy image.

According to a further exemplary embodiment of the invention, the method further comprises displaying the enhanced current fluoroscopy image, the first composite image and/or the second composite image via a display unit.

In other words, the method may comprise the following steps: acquiring an angiography data set containing information on an interventional device. This image sequence comprises frames with and without contrast agent. Furthermore, the method comprises acquiring a live fluoroscopic data set containing information on the interventional device; creating a vessel roadmap image by processing images of the angiography data set and/or previous images of the live fluoroscopic data set in such a way that the information on the interventional device is removed from the resulting vessel roadmap image; and combining the vessel roadmap image with a current image of the fluoroscopic data set.

According to a third aspect of the present invention, a computer program element is provided. The computer program element, when being executed by a processing unit, is adapted to carry out the method described above.

According to a forth aspect of the present invention, a computer readable medium having stored thereon a program element, as described above, is provided.

It has to be noted that features described with respect to the imaging system for automatic roadmapping for endovascular interventions as described above and in the following may be features of the method and vice versa.

These and other aspects of the invention will be apparent from and elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
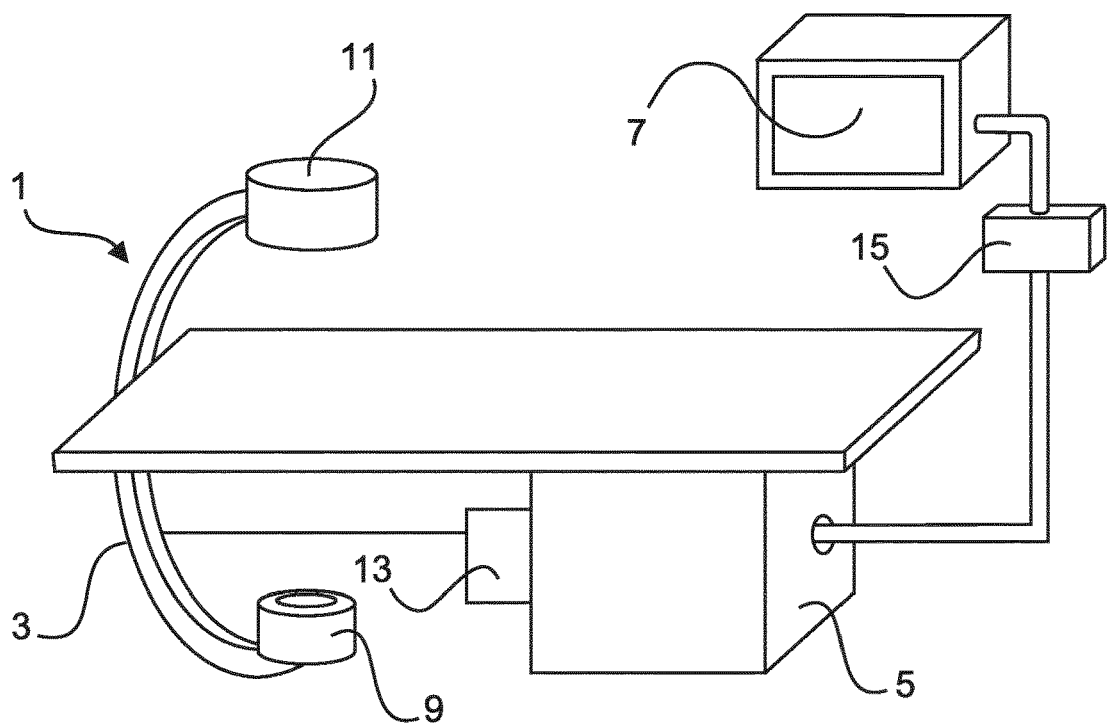
FIG. 1 shows an imaging system for automatic roadmapping for endovascular interventions according to an exemplary embodiment of the invention.

FIG. 1 schematically shows an imaging system 1 for automatic roadmapping for endovascular interventions. For example, the system 1 may be employed in a catheterization laboratory. The system 1 comprises an x-ray imaging device 3 for acquiring x-ray images. The imaging device 3 may comprise an x-ray radiation source 9 and an x-ray detection module 11. The x-ray detection module 11 may be positioned opposite the x-ray radiation source 9. During the examination and/or intervention procedure a subject such as a patient is located between the x-ray detection module 11 and the x-ray radiation source 9, e.g. on a table.

Furthermore, the imaging system 1 comprises a calculation unit 5 which may for example be a processor unit with a memory unit 13. Therein, the calculation unit 5 is adapted to execute an algorithm which may for example be stored on the memory unit 13. The calculation unit 5 is electrically and functionally connected to the x-ray imaging device 3.

Moreover, the imaging system 1 comprises a display unit 7 on which one or several images may be visualized. Therein, the display unit 7 may comprise one or several screens. A further component of the imaging system 1 is a user interface unit 15 by way of which a user such as a physician, particularly a cardiologist or a cardiac surgeon, may interact with the calculation unit 5 and the display unit 7. Therein, the display unit 7 as well as the user interface unit 15 are electrically and functionally connected to the calculation unit 5.

The imaging system 1 and the corresponding method for automatic roadmapping for endovascular interventions may for example be used in relation with stent placement, with replacement of the aortic valve or other types of heart valves, such as pulmonary, mitral and tricuspid valves and with aneurism treatment.

The x-ray imaging device 3 acquires a first x-ray image 21 and a second x-ray image 23 as shown in the following Figures. Therein, acquiring may denote detecting via the x-ray detection module 11, retrieving from the memory unit 13 or retrieving from an external data base or memory device. The first x-ray image 21 may be the first frame of an angiogram and particularly of an aortogram and may be acquired at a time 0 and denoted by $A_0$. Therein, in the first x-ray image 21 no contrast agent is present in the vessels 19. The second x-ray image 23 may be a frame of the angiogram subsequent to the first frame 21 and may be acquired at a time t and denoted by $A_t$. Therein, in the second x-ray image 23 contrast agent is present in the vessels 19. Moreover, in both images 21, 23 an interventional device 17 such as a wire is present in the vessels 19.

Figure 2:
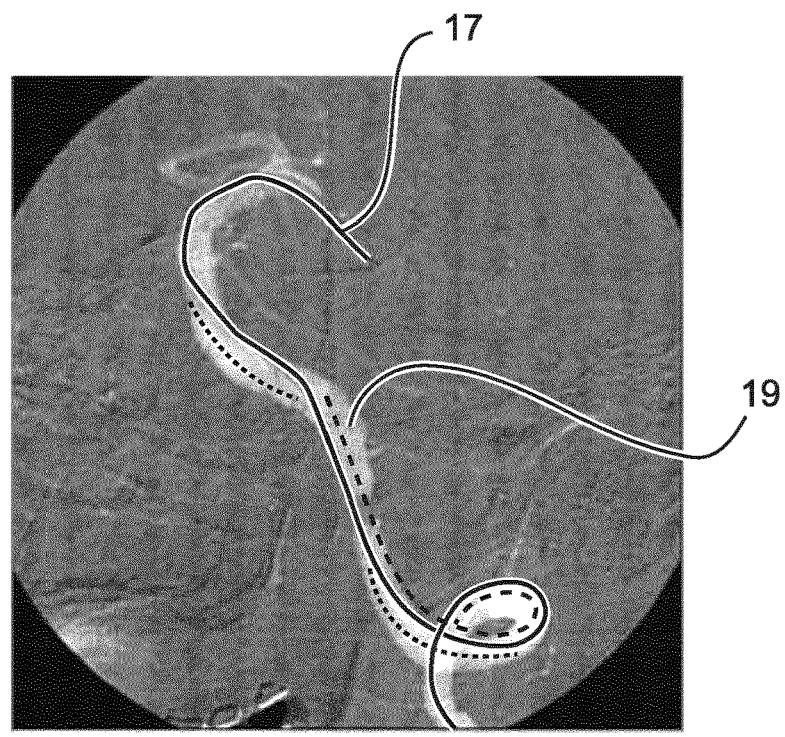
FIG. 2 shows an image which represents a vessel mask overlaid on a fluoroscopy image.

To provide information on the anatomy of the area of interest during endovascular examinations or interventions and at the same time reduce the amount of contrast agent employed, a mask image may be created by subtracting the first x-ray image 21 from the second x-ray image 23. Therein, the anatomy of the vessels 19 and the interventional device 17 are shown in FIG. 2. Background structures such as bones are removed from the image mask due to the subtraction. The result of such a subtraction may be overlaid to a fluoroscopy image as shown in FIG. 2. In FIG. 2 the vessels appear in white whereas the device appears in black.

However, due to motion, caused e.g. by breathing, the subtraction result shown in FIG. 2 contains artifacts. Some particularly disturbing artifacts are related to the interventional device 17. Particularly, the moving interventional device 17 generates a positive and a negative footprint in a mask image generated by subtraction. The negative footprint of the interventional device 17 is shown as a dotted line in FIG. 2. The positive footprint of the interventional device 17 is shown as a dashed line. Thus, in the overlay of the vessel mask with the fluoroscopy image the interventional device 17 may appear three times. Such artifacts may occlude the visualization of the area under examination and/or treatment. An overlay 39 of a subtraction result of first and second x-ray images 21, 23 with a current fluoroscopy image 31 is also shown in FIG. 3C. FIG. 3C shows similar artifacts as FIG. 2.

The imaging system 1 solves the problem of reducing the artifacts in the images by automatically minimizing, removing and/or wiping out the visibility of the interventional device 17 in the subtraction result. In this way a roadmap image 27, also denoted by $R_t$ without the interventional device is received. Therein, the automatic minimizing or removing of the interventional device 17 may be denoted as $W_1$, which stands for the operation, and not its results. Therein, the visibility of the interventional device 17 may be minimized by processing the first x-ray image 21 and the second x-ray image 23 before subtracting these images 21, 23. In this case this process may be denoted by $R_t=W_1(A_t)-W_1(A_0)$.

Alternatively, the visibility of the interventional device 17 is minimized by processing the roadmap image 27 after subtracting the first x-ray image 21 from the second x-ray image 23. In this case this process may be denoted by $R_t=W_1(A_t-A_0)$.

The subtraction of the first x-ray image 21 from the second x-ray image 23 may take place in the x-ray absorption domain. Therein, subtracting may comprise applying the logarithmic function to the image pixel values, forming the difference of the pixel values of the first and the second x-ray images and applying the exponential function to the result. Moreover, the processing of the images may comprise calculating a translation vector, or more generally a geometrical transform, between first and second x-ray images 21, 23 in order to account for possible motions between the two images.

The automatic minimizing of the visibility of the interventional device 17 may comprise an automatic detection of the interventional device 17 and further in-painting of the detected interventional device 17 in the first x-ray image 21, in the second x-ray image 23 and/or in the reference fluoroscopy image 23 by the calculation unit 5. Therein, in-painting may denote adapting or matching the interventional device 17 to the surroundings, or modeling or estimating the absorption of the device, and removing this modeled or estimated absorption over the device footprint. The automatic detection of the interventional device 17 may be based on the contrast value, on the geometry and/or on the kinetics of the interventional device 17. Therein, the elongated shape of the interventional device 17 and the restriction of the location and movement of the interventional device 17 to the inside of the vessels 19 may be used as input information.

Alternatively, automatically minimizing the visibility of the interventional device 17 may comprise filtering out details smaller than the vessels 19 in the first x-ray image 21, in the second x-ray image 23 and/or in the reference fluoroscopy image 23 by the calculation unit 5. For example, this may be realized by morphological filtering. Furthermore, the filtering may be restricted to the inside area of the vessels 19. For this purpose, the vessels 19 may automatically be detected and saturated in their representation.

Figure 3:
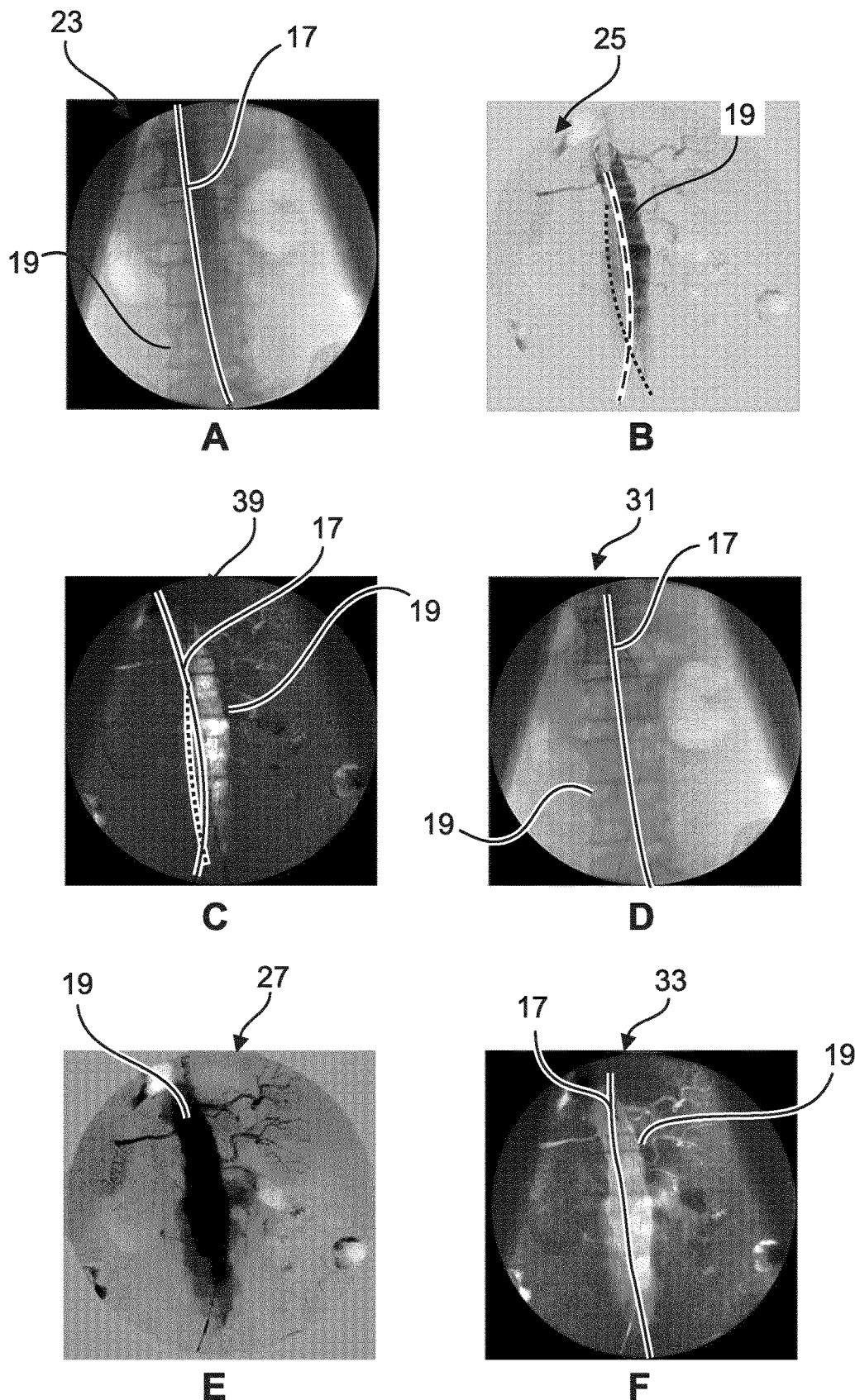
FIG. 3 shows different images used and generated by the imaging system of FIG. 1 in comparison to images generated by known systems.

FIG. 3 shows different images used and generated by the imaging system 1 of FIG. 1 in comparison to images generated by known systems. FIG. 3A shows a second x-ray image 23. A first x-ray image 21 is not presented in FIG. 3. However, the first x-ray image 21 represents for example the first frame of the angiography to which the second y-ray image 23 belongs and in which the contrast agent is not jet present in the area of interest.

FIG. 3B shows the subtraction result 25 of the first and the second x-ray images 21, 23 without the automatic minimization of the visibility of the interventional device 17. As explained in connection with FIG. 2, the subtraction result 25 shows the vessels 17, as well as a negative and a positive footprint of the interventional device 17 denoted by a dotted and by a dashed line.

FIG. 3E the visibility of the interventional device 17 is minimized in the subtraction result which provides a roadmap image 27 according to the invention. Therein, the roadmap image 27 only shows the saturated or filtered vessels 19 without the interventional device 17.

FIG. 3D shows the current or live fluoroscopy image 31 in which the vessels 19 as well as the current position of the interventional 17 are shown. The current fluoroscopy image may be denoted by Ft. However, the vessels are virtually invisible in the fluoroscopy image 31 since there is not contrast agent present.

The overlays of the current fluoroscopy image 31 with the different mask images as shown in FIG. 3B and FIG. 3E are respectively presented in FIG. 3C and in FIG. 3F. Therein, in FIG. 3C the overlay 39 of the subtraction result 25 of FIG. 3B with the current fluoroscopy image 31 of FIG. 3D is shown. This overlay 39 is relatively cluttered and shows three interventional devices 17. FIG. 3F shows an overlay of the roadmap image 27 of FIG. 3E with the current fluoroscopy image 31 of FIG. 3D. This overlay is denoted as first composite image 33 and only shows the current position of the interventional device 17. The representation in FIG. 3E provides a clearer visualisation of the area of interest which is not occluded by several footprints of the interventional device 17. The overlay shown in the composite image 33 may also be denoted by $Comb_1(F_t, R_t)$.

Figure 4:
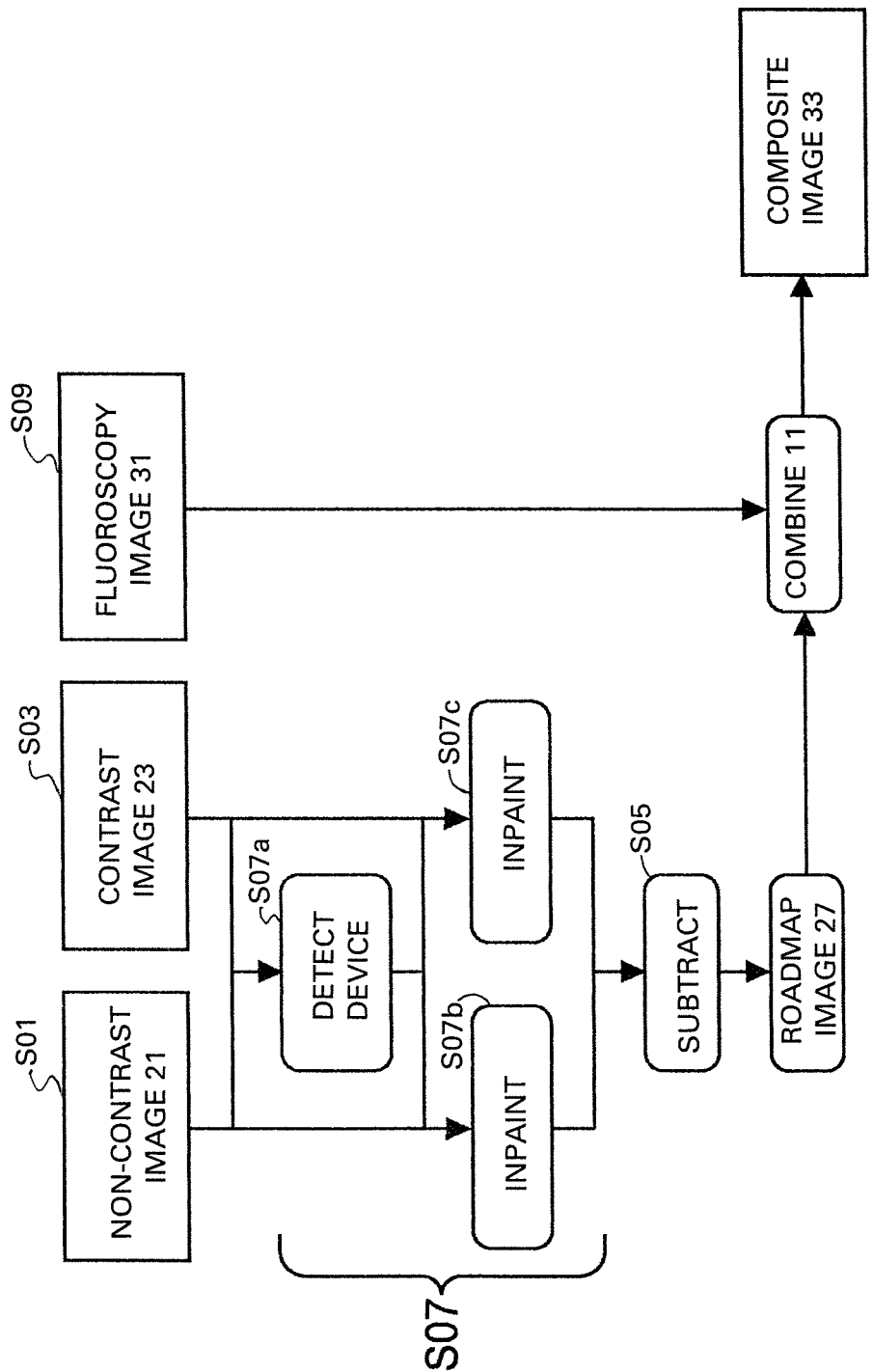
FIG. 4 schematically shows a flow chart of a method according to an exemplary embodiment of the invention.

FIG. 4 schematically shows a flowchart of the method for automatic roadmapping according to a first exemplary embodiment of the invention. In step S01 a first x-ray image 21 is acquired by the x-ray imaging device 3. Therein, in the first x-ray image 21 the interventional device 17 is present in the vessels 19 while no contrast agent is injected into the vessels 19, In step S03 a second x-ray image 23 is acquired by the x-ray imaging device 3. Therein, in the second x-ray image 23 the interventional device 17 is present in the vessels 19 while contrast agent is also present in the vessels 19. Steps S01 and S03 may correspond to the acquisition of an angiogram and particularly of an aortogram.

Subsequently, in step S07 the visibility of the interventional device 17 is minimized in the later created roadmap image 27 by the calculation unit 5. For this purpose in step S07a the interventional device 17 is automatically detected in the first and the second x-ray images 21, 23. The detection of the interventional device 17 may take place independently in both x-ray images 21, 23. Therein, for example radiopaque elongated objects are detected in the images 21, 23 and a mask indicating their position in the image may be created. Alternatively and more advantageously, the detection may take place jointly in both x-ray images 21, 23. Therein, the detection results of one of the images may be employed to simplify the detection of the interventional device 17 in the other image. Particularly, a matching between the images may be conducted assuming a limited motion of the interventional device 17 between the different frames. Furthermore, in step S07b the detected interventional device 17 is in-painted in the first x-ray image 21 and in step S07c the detected interventional device 17 is in-painted in the second x-ray image 23. The in-painting may be based on the devices location mask.

In step S05 which optionally may be executed before or after step S07 a roadmap image 27 is created by subtracting the first x-ray image 21 from the second x-ray image 23 by the calculation unit 5. Therein, the subtraction may be a subtraction between the two frames 21, 23. Alternatively, more advanced techniques, e.g. employing temporal integration could be used. Furthermore, in step S09 at least one current fluoroscopy image 31 is acquired with the interventional device 17 present in the vessels 19. Therein, the acquisition geometry is preferably the same during the angiography acquisition in steps S01, S03 and the fluoroscopy acquisition in step S09. In step S11 a first composite image 33 is generated by combining the roadmap image 27 with the at least one current fluoroscopy image 31.

If step S05 is executed before step S07, step S07 may be replaced by normalizing the subtracted image and saturating the main bulk of contrast agent corresponding to the region of interest, in order to obtain a fully transparent mask in that region.

Figure 5:
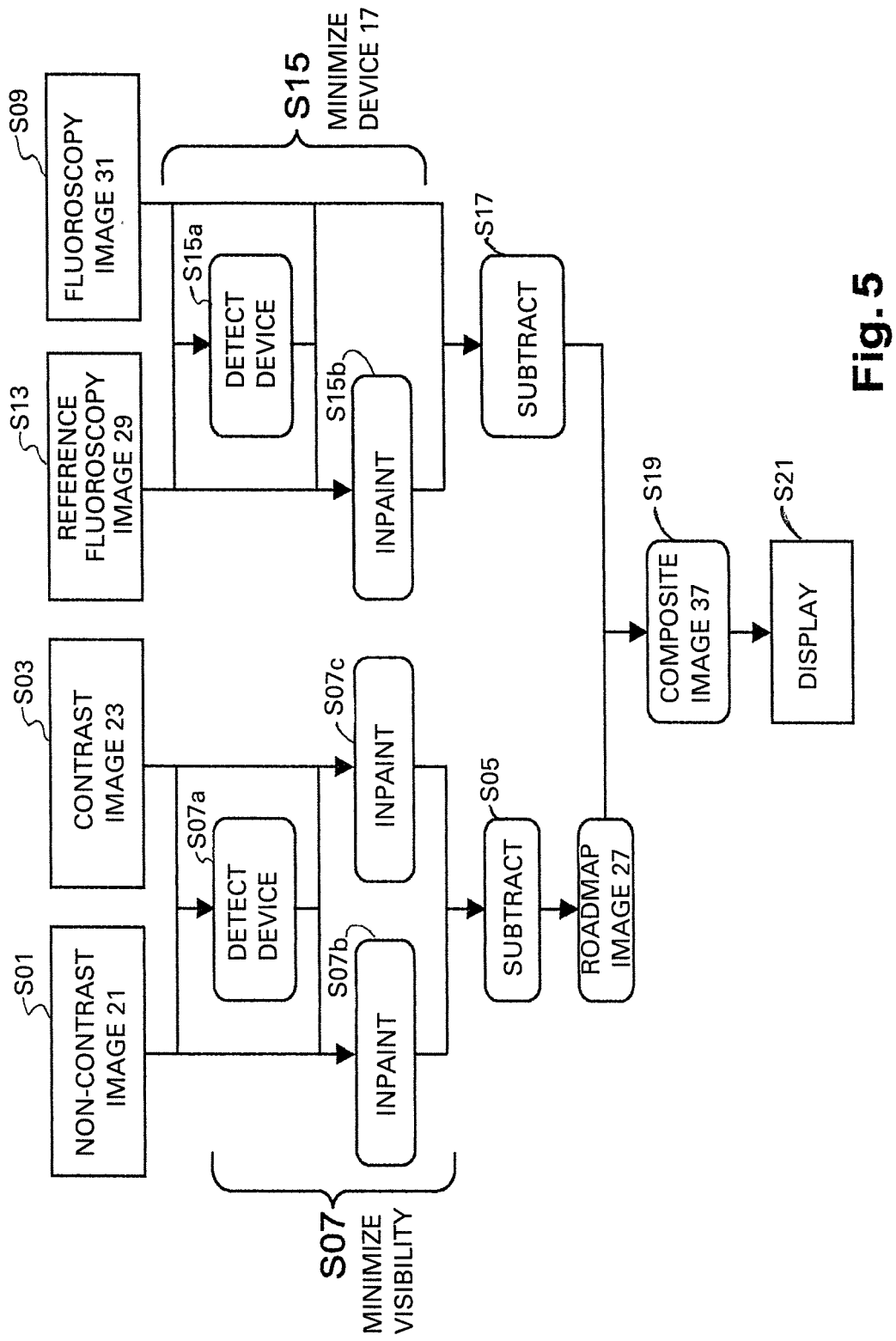
FIG. 5 schematically shows a flow chart of a method according to a further exemplary embodiment of the invention.

In FIG. 5 an alternative exemplary embodiment of the method for automatic roadmapping is shown as a flow chart. Therein, the embodiment shown in FIG. 5 comprises a double subtraction. Steps S01 to S11 are similar to the embodiment shown in FIG. 4. However, additionally the method shown in FIG. 5 comprises acquiring a reference fluoroscopy image 29 with the interventional device 17 present in the vessels 19 and no contrast agent present in the vessels 19 in step S13. Therein, the reference fluoroscopy image 29 may be a first frame of a sequence of live fluoroscopy images.

In step S15 the visibility of the interventional device 17 is automatically minimized in the reference fluoroscopy image 29 by the calculation unit 5. For this purpose, in step S15a the interventional device 17 is automatically detected in the reference fluoroscopy image 29 and possibly in the current fluoroscopy image 31 similarly to step S07a. Therein, the information contained in the current fluoroscopy image 31 may be used to enhance the detection of the interventional device 17 in the reference fluoroscopy image 29. In step S15b the detected interventional device 17 is in-painted in the reference fluoroscopy image 29.

In step S17 an enhanced current fluoroscopy image 35 is created by subtracting the reference fluoroscopy image 29 from the current fluoroscopy image 31 by the calculation unit 5. Steps S15 and S17 may vary in their order similarly to steps S05 and S07. Therein, the subtracting result, i.e. the enhanced current fluoroscopy image 35, may show only the interventional device 17 at time t. This may also be denoted as $D_t$. Using the nomenclature described above the process of generating the enhanced current fluoroscopy image 35 may be denoted as $D_t = F_t - W_2(F_0)$.

In step S19 a second composite image 37 is generated by combining the roadmap image 27 with the enhanced current fluoroscopy image 35. This process may be denoted as $Comb_2(R_t, D_t)$. Furthermore, in step S21 the enhanced current fluoroscopy image 35, the first composite image 33 and/or the second composite image 37 are displayed on the display unit 7.

It has to be noted that embodiments of the invention are described with reference to different subject matters. In particular, some embodiments are described with reference to method type claims whereas other embodiments are described with reference to the system type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

LIST OF REFERENCE SIGNS 1 imaging system
3 x-ray imaging device
5 calculation unit
7 display unit
9 x-ray radiation source
11 x-ray detection module
13 memory unit
15 user interface unit
17 interventional device (wire)
19 vessel (e.g. aorta)
21 first x-ray image
23 second x-ray image
25 subtraction result of first and second x-ray images
27 roadmap image
29 reference fluoroscopy image
31 current fluoroscopy image
33 first composite image
35 enhanced current fluoroscopy image
37 second composite image 39 overlay of subtraction result of first and second x-ray images with the current fluoroscopy image S01 acquiring a first x-ray image with an interventional device present in the vessels while no contrast agent is injected into the vessels S03 acquiring a second x-ray image with the interventional device present in the vessels while contrast agent is injected into the vessels S05 creating a roadmap image by subtracting the first x-ray image from the second x-ray image S07 automatically minimizing the visibility of the interventional device in the roadmap image S07a automatically detecting of the interventional device S07b in-painting the interventional device in the first x-ray image S07c in-painting the interventional device in the second x-ray image S09 acquiring at least one current fluoroscopy image with the interventional device present in the vessels S11 generating a first composite image by combining the roadmap image with the at least one current fluoroscopy image S13 acquiring a reference fluoroscopy image with the interventional device present in the vessels S15 automatically minimizing the visibility of the interventional device in the reference fluoroscopy image S15a automatically detecting of the interventional device in the reference fluoroscopy image and possibly in the current fluoroscopy image S15b in-painting the interventional device in the reference fluoroscopy image S17 creating an enhanced current fluoroscopy image by subtracting the reference fluoroscopy image from the current fluoroscopy image S19 generating a second composite image by combining the roadmap image with the enhanced current fluoroscopy image S21 displaying the enhanced current fluoroscopy image, the first composite image and/or the second composite image via a display unit

The invention claimed is:

1. An imaging system for automatic roadmapping for endovascular interventions, the system comprising:
   an x-ray imaging device configured to:
      acquire a first x-ray image of vessels with an interventional device present in the vessels while no contrast agent is injected into the vessels, and
      acquire a second x-ray image of the vessels with the interventional device present in the vessels while contrast agent is injected into the vessels; and
   a calculation unit configured to create a roadmap image by subtracting the first x-ray image from the second x-ray image with minimized visibility of the interventional device by:
      detecting the interventional device in the first and second x-ray images,
      inpainting the detected interventional device in the first x-ray image and the second x-ray image, and
      subtractively combining the first image with the interventional device inpainted and the second image with the interventional device inpainted to create the roadmap image with minimized visibility of the interventional device.

2. The system according to claim 1,
   wherein the x-ray imaging device is adapted for acquiring at least one current fluoroscopy image with the interventional device present in the vessels;
   wherein the calculation unit is adapted for generating a first composite image by combining the roadmap image with the minimized visibility of the interventional device and the at least one current fluoroscopy image.

3. The system according to claim 2,
   wherein the x-ray imaging device is adapted for acquiring a reference fluoroscopy image with the interventional device present in the vessels;
   wherein the calculation unit is adapted for automatically minimizing the visibility of the interventional device in the reference fluoroscopy image;
   wherein the calculation unit is adapted for creating an enhanced current fluoroscopy image by subtracting the reference fluoroscopy image from the current fluoroscopy image;
   wherein the calculation unit is adapted for generating a second composite image by combining the roadmap image with the enhanced current fluoroscopy image.

4. The system according to claim 3, further comprising:
   a display unit;
   wherein the display unit is adapted for displaying the enhanced current fluoroscopy image, the first composite image and/or the second composite image.

5. The system according to claim 1,
   wherein the automatic detection of the interventional device is based on the contrast value of the interventional device, on the geometry of the interventional device and/or on the kinetics of the interventional device.

6. A method for automatic roadmapping for endovascular interventions, the method comprising the following steps:
   acquiring a first x-ray image of vessels of a patient with an interventional device present in the vessels while no contrast agent is injected into the vessels;
   acquiring a second x-ray image of the vessels with the interventional device present in the vessels while contrast agent is injected into the vessels;
   creating a roadmap image by subtracting the first x-ray image from the second x-ray image;
   automatically minimizing the visibility of the interventional device in the roadmap image by one of:
      inpainting the interventional device out of the first and second images before subtracting, or
      inpainting the interventional device out of the roadmap image.

7. The method according to claim 6, further comprising:
   acquiring at least one current fluoroscopy image of the vessels with the interventional device present in the vessels;
   generating a first composite image by combining the roadmap image with the minimized visibility of the interventional device and the at least one current fluoroscopy image.

8. The method according to claim 7, further comprising:
   acquiring a reference fluoroscopy image of the vessels with the interventional device present in the vessels;
   automatically minimizing the visibility of the interventional device in the reference fluoroscopy image;
   creating an enhanced current fluoroscopy image by subtracting the reference fluoroscopy image from the current fluoroscopy image;
   generating a second composite image by combining the roadmap image with the enhanced current fluoroscopy image.

9. A computer program element, which, when being executed by a processing unit, is adapted to carry out the method of claim 6.

10. A non-transitory computer readable medium carrying a program, which, when executed by a processor controls the processor to carry out the method of claim 6.

11. A system for roadmapping endoscopic interventions in vessels of a patient, the system comprising:
one or more processors configured to:
receive a first contrast agent-free image of a portion of the vessels in which an endoscope is present,
receive a second contrast agent-enhanced image of the portion of the vessels in which the endoscope is present,
subtract the first and second images to generate a roadmap image,
matching a coloring of the endoscope with a color of the vessels surrounding the endoscope in (i) the roadmap image and/or (ii) the first and second images before subtracting, wherein a visibility of the endoscope in the roadmap image is minimized, and
control a display device to display the roadmap image with the visibility of the endoscope minimized.

12. The system according to claim 11, wherein the one or more processors are further configured to:
receive real-time fluoroscopy images of the portion of the vessels as the endoscope moves through the vessels; and
combine the roadmap image with the visibility of the endoscope minimized and the real-time fluoroscopic images.

13. The system according to claim 12, wherein the one or more processors are further configured to:
receive a reference fluoroscopic image; and
subtract the reference fluoroscopic image from the real-time fluoroscopic images.

14. The system according to claim 12, further including:
the display device.

15. The system according to claim 12, further including:
one or more diagnostic imaging devices configured to acquire the first image, the second image, and the real-time fluoroscopic images.

\* \* \* \* \*